United States Patent
Cabrera et al.

[19]

[11] Patent Number: 5,820,575
[45] Date of Patent: Oct. 13, 1998

[54] ABDOMINAL SUPPORT BELT

[75] Inventors: Juan Pablo Cabrera, San Antonio; Daniel Cabana, Garden Ridge, both of Tex.

[73] Assignee: Rooster Products International Inc., San Antonio, Tex.

[21] Appl. No.: 475,362

[22] Filed: Jun. 7, 1995

[51] Int. Cl.$^6$ ........................................... A61F 5/00
[52] U.S. Cl. ........................ 602/19; 2/235; 128/100.1
[58] Field of Search .................... 602/19; 2/311, 2/312; 128/96.1, 100.1, 101.1

[56] References Cited

U.S. PATENT DOCUMENTS

| | | |
|---|---|---|
| 2,104,699 | 1/1938 | O'Dell . |
| 3,441,027 | 4/1969 | Lehman . |
| 3,570,480 | 3/1971 | Stubbs . |
| 3,717,143 | 2/1973 | Johnson . |
| 3,920,008 | 11/1975 | Lehman . |
| 4,099,524 | 7/1978 | Cueman et al. . |
| 4,475,543 | 10/1984 | Brooks et al. . |
| 4,572,167 | 2/1986 | Brunswick . |
| 4,836,194 | 6/1989 | Sebastian et al. . |
| 4,964,401 | 10/1990 | Taigen . |
| 5,086,758 | 2/1992 | Schiek, Sr. et al. . |
| 5,111,806 | 5/1992 | Travis ....................................... 602/19 |
| 5,147,261 | 9/1992 | Smith et al. . |
| 5,205,815 | 4/1993 | Le Boennec et al. ..................... 602/19 |
| 5,267,948 | 12/1993 | Elliott ........................................ 602/19 |
| 5,302,171 | 4/1994 | Pearson et al. ........................... 602/19 |
| 5,334,134 | 8/1994 | Saunders ................................... 602/19 |
| 5,362,304 | 11/1994 | Varn ......................................... 602/19 |
| 5,387,183 | 2/1995 | Jones ........................................ 602/19 |
| 5,388,274 | 2/1995 | Glover et al. . |
| 5,499,965 | 3/1996 | Sanchez ................................... 602/19 |

*Primary Examiner*—Richard J. Apley
*Assistant Examiner*—Kim M. Lee
*Attorney, Agent, or Firm*—Jenkens & Gilchrist

[57] ABSTRACT

An abdominal support belt having an inner retainment strap for allowing the wearer to loosen the body of the belt while the retainment strap maintains the position of the belt against the wearer, under a tension less than that applied by the belt against the wearer when the belt is in a use position.

13 Claims, 1 Drawing Sheet

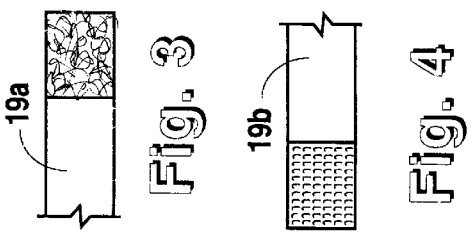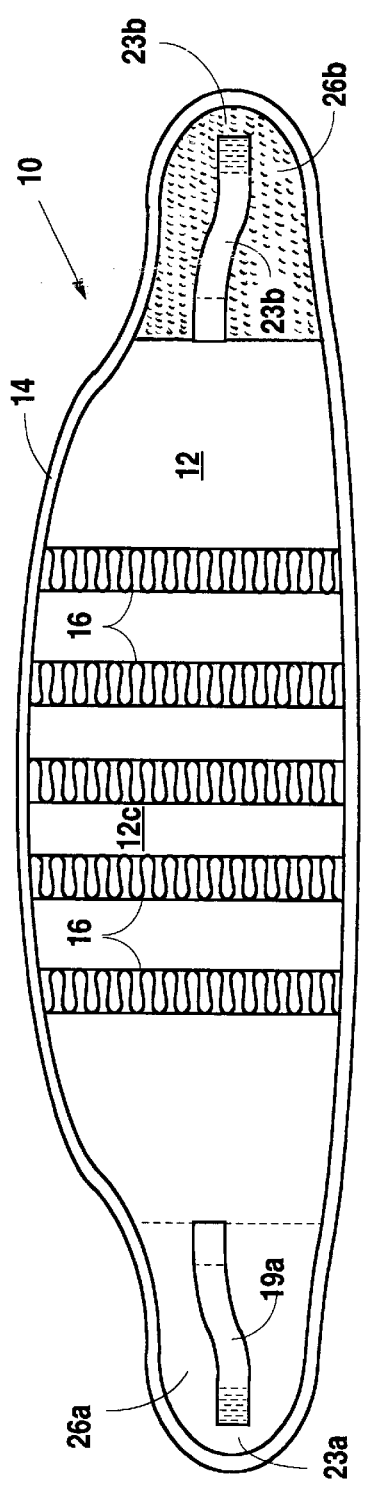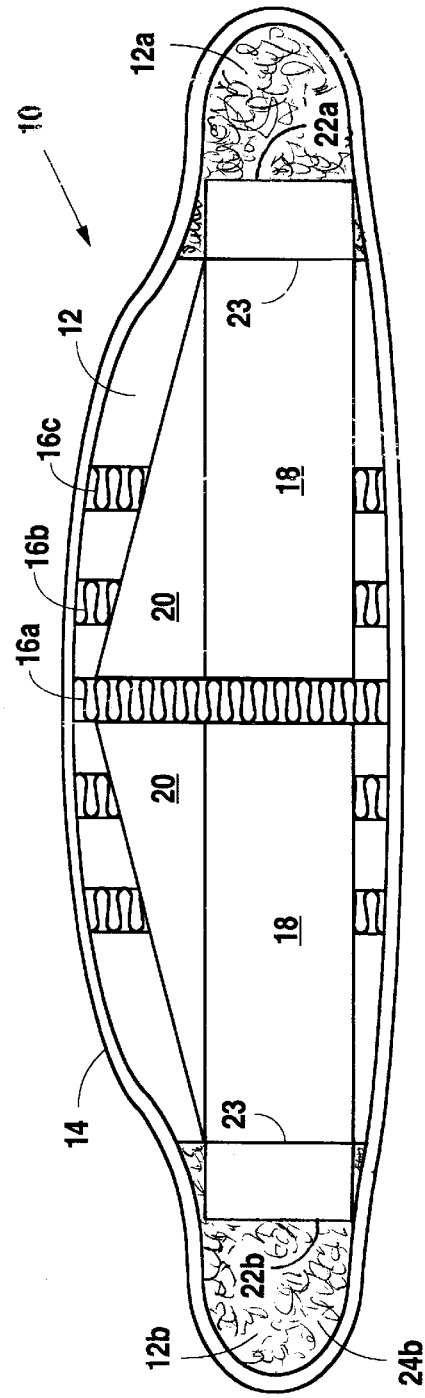

ABDOMINAL SUPPORT BELT

FIELD OF THE INVENTION

An abdominal support belt more specifically, an abdominal support belt having an inner retainment strap allowing the wearer to loosen the body of the belt while the retainment strap maintains the position of the belt on the wearer.

BACKGROUND OF THE INVENTION

Abdominal support belts are designed to provide the wearer, typically a manual laborer, with back and abdominal support during periods of lifting and standing. Typically, the abdominal support belt has an elastic body member with VELCRO® fasteners on either end allowing the wearer to wrap the belt around the small of his or her back and attach it at the front along his or her waistline. The belts sometimes have suspenders for allowing the wearer to loosen the belt during periods of nonuse without removing the belt. That is, during periods of nonuse when the worker does not want to remove it, the belt can hang from a pair of suspenders attached from the back of the belt to the front. The worker will typically, during periods of nonuse of the belt, simply undo the hook and loop closures from the front and allow the belt to hang, with the ends loose, from the suspenders.

Suspenders, however, have their disadvantages. While they allow the belt to hang loosely about the waist of the worker and in an unattached condition, it is easy for the straps to slip off the worker's shoulder. Further, the suspenders must be properly adjusted to the wearer, and they add additional time and expense to the manufacturing process. Last, suspenders can interfere with articles of clothing during movement of the shoulders of the wearer. Thus, utility lies in providing a retainment strap with the function of suspenders, without the disadvantages.

OBJECTS OF THE INVENTION

Thus, applicants seek in their abdominal support belt to provide structure which will maintain the abdominal support belt about the waist of the wearer, in a fashion that will not interfere with the normal function of the elastic bands of the abdominal support belt when it is in a use position, with the ends of the elastic band attached and the body of the abdominal support belt under tension, yet which will allow the user to undo the ends of the abdominal support belt of the strap and release tension from them, yet maintain the position of the abdominal support belt on the wearer. Moreover, applicants seek to provide in an elastic inner retainment strap all of the utilities of the suspenders without the inconveniences thereof.

SUMMARY OF THE INVENTION

Applicants provide for these advantages and others, which will be readily apparent from a review of the specifications, claims and drawings set forth herein, in a retainment strap having an inner retainment strap underlying the end portions of the body of the strap, the inner retainment strap maintaining the strap under tension against the body of the user, yet capable of relaxing when the strap is attached to the user in a condition under tension and capable of taking up the tension of the strap against the user when the strap is in a relaxed position.

BRIEF DESCRIPTION OF THE DRAWINGS

FIG. 1 is a elevational view of the inner surface of an elastic retainment strap.

FIG. 2 is an elevational view of the outer surface of an elastic retainment strap.

FIGS. 3 and 4 are bottom elevational views of the removed ends of the retainment straps of applicant's present invention.

DETAILED DESCRIPTION OF THE PREFERRED EMBODIMENT

FIGS. 1, 1a and 2 illustrate elastic abdominal belt (10) comprising a shell (12), typically nylon mesh. The shell has end portions (12a) and (12b) and a body portion (12c) located between the two removed ends. Piping (14), typically elastic, is sewn to the perimeter of shell (12). Abdominal belt (10) is designed to wrap around the waist of the wearer with a portion of the body portion (12c) laying against the small of the back. Body (12c) contains stiff, typically plastic, stays (16) oriented vertically with the longitudinal axis of belt (10). Stays (16) prevent the body of abdominal belt (10) from collapsing or curling up and provide additional support. Stays (16) include a central or main stay (16a) as well as a pair of inner stays (16b) and a pair of outer stays (16c). The stays are covered with a tough, durable fabric material, such as nylon, and sewn to the body of the abdominal belt.

Also sewn to the body, typically at central stay (16a) are a lower elastic band (18) and an upper elastic band (20). These bands are typically about four inches wide and, being elastic, can stretch from a relaxed position to a secured or tensioned position. The two elastic bands are typically oriented in the "V" pattern, as illustrated in FIG. 2, with the removed ends of the elastic bands coming together at end pads (22a) and (22b), respectively. The outer surfaces (23) of the end pads (22a) and (22b) are typically leather or some other suitable material. Located on the outer surfaces of end portion (12a) and end portion (12b) are first closure mating surface (24a) and second closure mating surface (24b). Typically, these closure surfaces are hook and loop-type, with the underside of pads (22a) and (22b) being the respective mating closure surfaces (24a) and (24b) for matting to pad ends (22a) and (22b), respectively. Thus, pad ends (22a) and (22b) can be attached adjustably to end portion (12a) and end portion (12b), respectively, along first closure mating surface (24a) and second closure mating surface (24b), respectively. It is noted that this can be adjustable so the tension of the belt against the wearer is adjustable. That is, pads (22a) and (22b) can be adjustably located longitudinally along end portions (12a) and (12b) to adjust the tension on abdominal belt (10) against the wearer. The closer pads (22a) and (22b) are to center stay (16a), the less tension the strap exerts against the wearer, the closer the pads are to the ends of the strap, the tighter the strap will be against the wearer.

FIG. 1 illustrates the inner surface of the belt, and it is seen how end portions (12a) and (12b) have respectively a plain end (26a) and a closure end mating surface (26b). Closure end mating surface (26b) is designed to overlap end portion (12a) such that first closure mating surface (24a) underlies closure end (26b).

When abdominal belt (10) is in use, lower elastic (18) and upper elastic (20) have been adjusted to proper tension by locating pads (22a) and (22b) at the desired location at or near ends (24a) and (24b). With the user grasping end portion (12a) and end portion (12b), the belt is pulled around the back of the user to the front with end portion (12b) overlapping end portion (12a), putting tension on the back of the belt against the user.

Applicants' elastic abdominal belt (10), however, has an additional feature. Namely, applicants' abdominal belt (10) has, securely attached to the inner surface of the shell, an inner retainment strap, typically elastic, and typically comprising an inner strap first section (19a) and inner strap second section (19b), each of the two sections with an attached end (21) securely affixing the section to the inner surface near or at the removed end portions (12a) and (12b), respectively. Each of the sections has free or removed ends (25a) and (25b), respectively, the free ends capable of being overlapped and having closure mating surfaces, typically of the hook and loop type, on the ends thereof such that the free ends (25a) and (25b) may overlap and attach adjustably.

The function of the inner retainment strap of applicants' abdominal support belt is to secure, under tension, shell (12) snugly to the wearer's body so that it does not droop, climb up, or fall off the wearer while the belt is in a loose, non-use condition. Thus, the inner retainment strap of applicants' present invention allows the wearer to secure abdominal belt (10) to the wearer without having to attach end portions (12a) and (12b). Moreover, the elastic nature of the inner retainment strap, along with its location and the adjustable feature, allows the wearer to adjust the belt (10) against his or her body with a tension less than that required for proper support. That is, the inner retainment strap of applicants' present invention allows the wearer to adjust the tension of the belt sufficient to locate the belt to the wearer, but while leaving end portions (12a) and (12b) unattached or in a relaxed position.

FIGS. 3 and 4 illustrate the removed ends (25a) and (25b) of the retainment strap sections (19a) and (19b). More specifically, FIGS. 3 and 4 illustrate the use of a hook and loop closure system on the removed ends of the inner retainment strap. Because the hook and pile is located along from about 1 inch up to a 4 inch portion, respectively, of the removed ends of the straps, they can be adjustably located to the comfort of the wearer.

Typically, the abdominal support belt of applicants' present invention comes in three sizes: Small (22"–32" waist); Medium (33"–42" waist); and Large (42"+ waist). The bodies of the shells are in different lengths, smallest having the shortest longitudinal distance between the removed ends and the largest having the greatest, the range being generally from 22" to 54". The inner retainment straps for each of the following are located approximately 6–8 inches inward from the removed ends. The length of each strap section in an unstretched condition is about 4–7 inches between the point of attachment and the removed end (typically 6 inches). The typical width of the inner retainment strap is 1½ inches. In the stretched condition, the length of each strap is up to 11 inches.

Thus, the worker can wear applicants' belt in comfort, without the use of clumsy suspenders, while removed end portions (12a) and (12b) remain either detached from one another or in a substantially loosened position. Simply put, there are many times when the wearer, for comfort or other reasons, would like to relax the tension normally applied to his or her body while the abdominal belt is in the use position with the elastic bands properly located and the first end and the second end overlapping and securely fastened. With applicants' invention, rather than removing the belt entirely, the worker is provided with the alternative of leaving the belt on, but having it either with the ends completely free or loose. This option is provided with applicants' inner retainment strap, which will remain secured with the free ends attached one to the other, creating sufficient tension in the belt to maintain the belt's location approximal to the wearer.

Terms such as "left," "right," "up," "down," "bottom," "top," "front," "back," "in," "out," and like are applicable to the embodiments shown and described in conjunction with the drawings. These terms are merely for purposes of description and do not necessarily apply to the position or manner in which the invention may be constructed for use.

Although the invention has been described in connection with the preferred embodiment, it is not intended to limit the invention's particular form set forth, but on the contrary, it is intended to cover such alternatives, modifications, and equivalences that may be included in the spirit and scope of the invention as defined by the appended claims.

What is claimed is:

1. An abdominal back support belt comprising:

an elastic shell having a body portion with an inner surface designed to lay against the body of a wearer and an outer surface, said shell for substantially surrounding the waist of the wearer when in a stretched condition, said shell further having two end portions, the end portions capable of overlapping and engaging one another; and inner retainment means located on the inner surface of said shell, said means being fixedly attached to said shell and entirely underlaying the shell when the shell is surrounding the waist of the wearer for releasably securing said belt to the wearer when said shell is in a relaxed condition, the relaxed condition applying less pressure to the waist of the wearer than the stretched condition;

wherein said means is capable of preventing the belt from falling off the wearer when said shell is released from the stretched condition.

2. The back support belt of claim 1, wherein said means includes hook and loop closures.

3. The back support belt of claim 1, wherein said means comprises a first strap portion and a second strap portion, the two strap portions each having removed ends capable of releasably attaching one to the other.

4. The back support belt of claim 3, wherein the first and the second strap portions are fixedly attached at their near ends to said elastic shell.

5. The back support belt of claim 1, wherein said means comprises a first elastic strap portion and a second elastic strap portion, the two elastic strap portions each having a near end fixedly attached to said shell and a removed end, the removed ends for releasably attaching one to another.

6. The back support belt of claim 5, wherein the removed ends of the two elastic strap portions are capable of releasably attaching one to the other through the use of hook and loop closures.

7. The back support belt of claim 5, wherein the two elastic strap portions, when in a relaxed condition, do not extend beyond the end portions of said elastic shell and when in a stretched condition are capable of extending beyond the end portion of said elastic shell.

8. A back support belt comprising a shell having a body portion, the shell including two end portions, the body portion of said shell including a multiplicity of vertically oriented stays, said shell including a multiplicity of elastic waist bands secured near a central portion of the body, the multiplicity of elastic waist bands for removably attaching at removed ends thereof to the end portion of the body so as to adjust the tension in the shell;

attachment means to engage the removed ends of the multiplicity of elastic waist bands one to another such that the elastic waist bands are under tension and the belt is engaged with the wearer; and a retainment strap fixedly attached to the inner surface of the body of said shell to underlay the removed ends of said shell when the removed ends of said shell are attached, one to the other, and the multiplicity of elastic waist bands are under tension and to retain, under tension, the belt to the wearer when removed ends of said shell are disengaged.

9. The back support belt of claim 8, wherein said retainment strap is comprised of a first section and second section.

10. The back support belt of claim 9, wherein the two sections of said retainment strap each have a near end fixedly attached to the shell and removed ends, the removed ends of said two sections having means to adjustably and releasably attach one to the other.

11. The back support belt of claim 10, wherein the two sections of said retainment strap are made of elastic bands.

12. The back support belt of claim 11, wherein the means to releasably and adjustably attach the removed ends of said retainment strap one onto the other is hook and loop fasteners.

13. A method of attaching an abdominal support belt to the body of a wearer, the support belt having an elastic body with end portions and a fixedly attached inner retainment strip having removed ends, said strap entirely underlaying the end portions of said body when the end portions are attached, one to another, comprising the steps of;

first attaching the inner retainment strap around the body of the wearer by securing the removed ends such that the abdominal support belt exerts a first tension against the body of the user, the first tension being sufficient to generally retain the support belt to the body of the wearer; and second attaching the abdominal support belt to the torso of the wearer by securing said end portions such that the support belt exerts a second tension against the body of the wearer, the second tension being greater than the first tension and sufficient to provide abdominal support to the wearer.

* * * * *